US005665554A

United States Patent [19]

Reeve et al.

[11] Patent Number: 5,665,554
[45] Date of Patent: Sep. 9, 1997

[54] MAGNETIC BEAD PRECIPITATION METHOD

[75] Inventors: Michael Alan Reeve, Oxon; Philip Steven Robinson, Bucks, both of United Kingdom

[73] Assignee: Amersham International PLC, Buckinghamshire, United Kingdom

[21] Appl. No.: 737,220

[22] PCT Filed: Jun. 9, 1995

[86] PCT No.: PCT/GB94/01365

§ 371 Date: Nov. 14, 1996

§ 102(e) Date: Nov. 14, 1996

[87] PCT Pub. No.: WO95/33827

PCT Pub. Date: Dec. 14, 1995

[30] Foreign Application Priority Data

Jun. 9, 1994 [GB] United Kingdom ............... 9411572

[51] Int. Cl.$^6$ ............................................... C12Q 1/68
[52] U.S. Cl. ........................... 435/6; 435/270; 436/526; 209/214; 210/695; 210/222
[58] Field of Search ................... 435/6, 270; 436/526; 209/214; 210/695, 222

[56] References Cited

FOREIGN PATENT DOCUMENTS

WO 91/12079  8/1991  WIPO.

OTHER PUBLICATIONS

Alderton et al., "Magnetic Bead Purification of M13 DNA Sequencing Templates," *Analytical Biochemistry*, vol. 201, pp. 166–169 (1992).

Richard K. Wilson, "High–Throughput Purification of M13 Templates for DNA Sequencing," *BioTechniques*, vol. 15, No. 3, pp. 414, 416, 418, 420, and 422 (1993).

*Primary Examiner*—James C. Housel
*Assistant Examiner*—Susan C. Wolski
*Attorney, Agent, or Firm*—Marshall, O'Toole, Gerstein, Murray & Borun

[57] ABSTRACT

A method of recovering a first material, e.g. plasmid DNA, from a solution containing pre-precipitated second material, e.g. genomic DNA and cellular debris, by precipitating the first material in the presence of magnetically attractable beads which become non-specifically associated with the newly formed precipitate, using a magnet to draw down the beads and the newly formed precipitate, and removing the supernatant.

7 Claims, No Drawings

MAGNETIC BEAD PRECIPITATION METHOD

WO91/12079 describes a method of recovering a biopolymer from solution which involves the use of magnetically attractable beads which do not specifically bind the polymer. The beads are suspended in the solution. Then the polymer is precipitated out of solution and becomes non-specifically associated with the beads. When the beads are magnetically drawn down, the polymer is drawn down with them. The polymer can subsequently be resolubilised and separated from the beads.

The present invention is a development of that technique. It is based on the surprising observation that the act of drawing down the magnetically attractable beads, which does bring down the precipitated polymer non-specifically associated with the beads, does not bring down an aggregated precipitate of a polymer which was present in the starting liquid prior to addition of the beads. In other words, it is the act of precipitating a polymer out of solution in the presence of the magnetically attractable beads that causes the polymer to entrap and become associated with the beads. This discovery is potentially useful in several circumstances, of which two are discussed here:

(i) Plasmid preparation from bacterial host cells is a technique that has found widespread usage in many areas within Molecular Biology [1].

In the following, the term "plasmid" is taken to include all double stranded DNA species that exist as supercoiled entities within bacterial host cells. Cosmids [2] are just one of many examples which will be obvious to those skilled in the art.

Current methods for plasmid preparation rely upon the removal (or destruction) of all of the undesired material present within a lysate of the plasmid-containing bacterial cells. Two main methods are in common usage. The first method, often referred to as "alkaline lysis" [3], relies upon the precipitation of a detergent complex of many of the undesired materials by high salt. This precipitation is followed by alcohol precipitation of the plasmid DNA. The second method, often referred to as "the boiling method" [4], relies upon the physical removal of viscous bacterial chromosomal and cellular material with a toothpick (or similar implement) followed by alcohol precipitation of the plasmid DNA.

Both of the above methods suffer from being difficult to automate and the "alkaline lysis" method also suffers from the inconvenience of having to transfer the supernatant to a fresh tube after the high salt precipitation step.

(ii) Proteins are routinely precipitated out of solution using ammonium sulphate, with some proteins requiring smaller concentrations of ammonium sulphate for precipitation. Thus for example, 30% ammonium sulphate can be added to precipitate some proteins present in a starting solution; later the ammonium sulphate concentration can be raised to 50% in order to precipitate the other proteins. As a technique for recovering these other proteins, this has the disadvantage that the supernatant needs to be transferred to a fresh tube after the first precipitation step.

The present invention addresses these problems. It has the advantage that the second precipitate can be recovered without the need to transfer the supernatant to a fresh tube after the first precipitation step. The invention is quick to perform and lends itself ideally to automation.

The invention provides a method of recovering a first molecular species from a starting liquid containing in solution the first molecular species in admixture with a second molecular species, which method comprises the steps of:

precipitating the second molecular species to form an aggregated precipitate of the second molecular species in the liquid, adding magnetically attractable beads to form a suspension of the beads in the liquid, precipitating the first molecular species to form an aggregated precipitate of the first molecular species which entraps the magnetically attractable beads, applying a magnetic field to draw down the magnetically attractable beads and the associated aggregated precipitate of the first molecular species, removing the supernatant liquid containing the aggregated precipitate of the second molecular species.

So far as the nature of the first and second molecular species are concerned, the invention is of general application. The first and second molecular species may be proteins with different salting out points. Preferably the first and second molecular species comprise plasmid DNA and chromosomal DNA.

First, a precipitation reagent is added so as to cause the second molecular species to form an aggregated precipitate in the liquid medium. The nature of the precipitation reagent and the conditions are conventional.

Second, magnetically attractable beads are added to form a suspension of the beads in the liquid. The nature of the magnetically attractable beads (hereinafter magnetic beads) is not material to the invention. But they do not carry on their surface a reagent which binds either the first or the second molecular species. The magnetic beads do not become associated with the pre-formed aggregated precipitate of the second molecular species.

Third, a different precipitation reagent (or the same precipitation reagent at a different concentration) is added to form an aggregated precipitate of the first molecular species which entraps and becomes associated with the magnetic beads. The nature of this precipitation reagent is not material to the invention. It may be added to the liquid either together with or after the magnetic beads. It is merely important that the precipitation of the first molecular species should take place in the presence of the magnetic beads so that the aggregated precipitate entraps and becomes associated with the beads.

Fourth, a magnetic field is applied to draw down a pellet comprising the magnetic beads and the associated aggregated precipitate of the first molecular species. Then the supernatant liquid containing the aggregated precipitate of the second molecular species is removed. Then the precipitate of the first molecular species may be washed, and resuspended in a liquid medium in which it is soluble, and the magnetic beads drawn down leaving the first molecular species in solution. The first molecular species remains in the same vessel throughout, and the whole operation is easily automated.

In a preferred embodiment, the method of the invention starts with a culture of plasmid-containing bacterial host cells. The culture may be used as such, or may be centrifuged and re-suspended in more concentrated form.

Alkali alone (e.g. sodium hydroxide) or alkali and detergent (e.g. sodium hydroxide and aqueous sodium N-lauroylsarcosine or sodium hydroxide and aqueous sodium dodecyl sulphate) are mixed with plasmid-containing bacterial host cells in a reaction tube. The alkali alone or the alkali and detergent lyse(s) the plasmid-containing bacterial host cells.

A salt (e.g. low pH sodium acetate, low pH potassium acetate or ammonium acetate) is added to the alkali, (detergent) and lysed plasmid-containing bacterial host cells. The salt causes the released bacterial chromosomal DNA to be precipitated out of solution. The precipitated bacterial chromosomal DNA then aggregates.

A nucleic acid precipitation reagent (e.g. isopropanol, ethanol or polyethylene glycol in aqueous sodium chloride) containing magnetic beads (e.g. FMP particles, Amersham International plc.) is then added to the salt-treated lysate of the plasmid-containing bacterial host cells. The nucleic acid precipitation reagent causes the plasmid DNA and bacterial RNA to be precipitated out of solution. The precipitated plasmid DNA and bacterial RNA then aggregate. This aggregation causes the passive entrapment of any magnetic particles within the vicinity of the aggregating species.

A magnetic field is then applied to the tube and contents.

The supernatant (containing aggregated bacterial chromosomal DNA) is discarded to waste.

The magnetic field is then removed from the tube.

The magnetically attractable pellet of aggregated plasmid DNA and bacterial RNA is then washed in 70% ethanol.

A magnetic field is again applied to the tube and contents.

The supernatant is discarded to waste.

The precipitated, 70% ethanol washed and still aggregated plasmid DNA associated with the magnetic beads by passive entrapment is then washed from the magnetic beads by resuspension in a medium (e.g. water or TE buffer) wherein the plasmid DNA is soluble. Remaining bacterial RNA is also washed from the magnetic beads under these conditions. This residual bacterial RNA can, however, be readily treated with ribonuclease so as to reduce it to low molecular weight fragments which stain only weakly on agarose gel analysis.

A magnetic field is again applied to the tube and contents.

The supernatant (containing plasmid DNA free from contaminating bacterial chromosomal DNA) is then transferred to another tube (or directly into a DNA sequencing reaction).

It is not easy by conventional methods to recover plasmid DNA from a solution that contains bacterial chromosomal and cellular material in suspension. The suspended precipitate containing bacterial chromosomal and cellular material is sticky and viscous and difficult to handle; it is also generally present in much larger amount than the plasmid DNA, typically three times the amount. So the use of magnetic beads in the precipitation and recovery in excellent yield of plasmid DNA from this messy mixture is quite striking. Once the recovery of plasmid DNA in this way has been demonstrated (see the Example below), it is plausible that the technique will be effective to precipitate and recover any first molecular species from a solution containing a preformed precipitate of any second molecular species.

EXAMPLE 1

The following experiment both illustrates this invention and demonstrates the need for magnetic beads in this invention.

Samples 1 and 2

500 μl of HB101 cells containing pBluescript were mixed with 25 μl of 2M NaOH and then 25 μl of 10% (w/v) aqueous sodium dodecyl sulphate. The samples were left for 1 minute at room temperature. 100 μl of 4.5M sodium acetate (pH 4.8) were then mixed with the cell lysate by vortexing. 550 μl of 1 mg/ml FMP particles (Amersham International plc.) in isopropanol were then mixed with the salt-treated cell lysate by pipetting up and down. The samples were left for 5 minutes at room temperature. The samples were placed on a Dynal MPC separator for 2 minutes and the supernatants were then removed using a vacuum aspirator. The samples were removed from the magnetic separator and washed with 500 μl of 70% ethanol by pipetting up and down. The samples were again placed on a Dynal MPC separator for 2 minutes and the supernatants were once more removed using a vacuum aspirator. The samples were removed from the magnetic separator and the pellets were resuspended in 50 μl of TE buffer [1] containing 0.1 mg/ml RNase by pipetting up and down. The samples were finally placed on a Dynal MPC separator for 2 minutes and the supernatants were transferred to a fresh tube using a pipette. The 50 μl of sample was mixed with 20 μl of gel loading dye [1] and 20 μl loaded on a 1% agarose gel prestained with ethidium bromide.

Samples 3 and 4

500 μl of HB101 cells containing pBluescript were mixed with 25 μl of 2M NaOH and then 25 μl of 10% (w/v) aqueous sodium dodecyl sulphate. The samples were left for 1 minute at room temperature. 100 μl of 4.5M sodium acetate (pH 4.8) were mixed with the cell lysate by vortexing. 550 μl of isopropanol were then mixed with the lysed cells by pipetting up and down. The samples were left for 5 minutes at room temperature. The samples were centrifuged for 10 minutes and the supernatants were then removed using a vacuum aspirator. The samples were washed with 500 μl of 70% ethanol by vortex mixing. The samples were again centrifuged for 10 minutes and the supernatants were once more removed using a vacuum aspirator. The samples were finally resuspended in 50 μl of TE buffer [1] containing 0.1 mg/ml RNase by extensive vortex mixing and heating to 60 degrees. The 50 μl of sample was mixed with 20 μl of gel loading dye [1] and 20 μl loaded on a 1% agarose gel prestained with ethidium bromide.

Samples 5 and 6

500 μl of HB101 cells containing pBluescript were centrifuged for 5 minutes. The supernatants were discarded to waste and the pellets were resuspended in 200 μl of TE buffer [1]. 200 μl of 0.2M NaOH, 1% (w/v) aqueous sodium dodecyl sulphate were then mixed with the resuspended cells. The samples were left for 1 minute at room temperature. 100 μl of 4.5M sodium acetate (pH 4.8) were then mixed with the cell lysate by vortexing. 550 μl of 1 mg/ml FMP particles (Amersham International plc.) in isopropanol were then mixed with the salt-treated cell lysate by pipetting up and down. The samples were left for 5 minutes at room temperature. The samples were placed on a Dynal MPC separator for 2 minutes and the supernatants were then removed using a vacuum aspirator. The samples were removed from the magnetic separator and washed with 500 μl of 70% ethanol by pipetting up and down. The samples were again placed on a Dynal MPC separator for 2 minutes and the supernatants were once more removed using a vacuum aspirator. The samples were removed from the magnetic separator and the pellets were resuspended in 50 μl of TE buffer [1] containing 0.1 mg/ml RNase by pipetting up and down. The samples were finally placed on a Dynal MPC separator for 2 minutes and the supernatants were transferred to a fresh tube using a pipette. The 50 μl of sample was mixed with 20 μl of gel loading dye. [1] and 20 μl loaded on a 1% agarose gel prestained with ethidium bromide.

Samples 7 and 8

500 μl of HB101 cells containing pBluescript were treated as described on pages 1.25 to 1.28 of reference 1 with final resuspension 50 μl of TE buffer [1] containing 0.1 mg/ml RNase by vortex mixing. The 50 μl of sample was mixed with 20 μl of gel loading dye [1] and 20 μl loaded on a 1% agarose gel prestained with ethidium bromide.

Results

Samples 1 and 2 illustrate the method of this invention using a starting culture of bacterial host cells. The plasmid DNA was clearly visible on the gel.

Samples 3 and 4 were obtained similarly but without using magnetically attractable beads, and are included for purposes of comparison. The gel showed a mess of genomic DNA.

Samples 5 and 6 are similar to samples 1 and 2, but obtained using a centrifuged and concentrated suspension of the starting bacterial host cells. Plasmid DNA without genomic DNA was clearly visible on the gel.

Samples 7 and 8 were obtained using a conventional method that involves transferring a liquid containing the plasmid DNA from one tube to another. This inconvenient method gave results similar to those of Samples 1, 2, 5 and 6.

EXAMPLE 2

The following experiment demonstrates both that the current invention is capable of automation and that strand separated plasmid (a better template for DNA sequencing, in many cases) can also be obtained simply by increasing the concentration of alkali used for lysis of the plasmid-containing bacterial host cells:

Samples 1, 2, 5, 6, 9, 10, 13 and 14

All samples were processed completely automatically using a DNA Sequencing Robot (Amersham International plc., Pilot Series Instrument running under Version 1.0 Software).

500 μl of HB101 cells containing pBluescript were mixed with 25 μl of 2M NaOH and then 25 μl of 10% (w/v) aqueous sodium dodecyl sulphate. 100 μl of 4.5M sodium acetate (pH 4.8) were then mixed with the cell lysate. 550 μl of 1 mg/ml FMP particles (Amersham International plc.) in isopropanol were then mixed with the salt-treated cell lysate. The samples were left for 5 minutes at room temperature. The samples were then magnetically separated and the supernatants were then removed to waste. The samples were washed with 500 μl of 80% ethanol. The samples were again magnetically separated and the supernatants were once more removed to waste. The samples were resuspended in 50 μl of TE buffer [1] containing 0.1 mg/ml RNase. The samples were finally magnetically separated and the supernatants were transferred to a microtitre plate. The 50 μl of sample was mixed with 20 μl of gel loading dye [1] and 20 μl loaded on a 1% agarose gel prestained with ethidium bromide.

Samples 3, 4, 7, 8, 11, 12, 15 and 16

All samples were processed completely automatically using a DNA Sequencing Robot (Amersham International plc., Pilot Series Instrument running under Version 1.0 Software).

500 μl of HB101 cells containing pBluescript were mixed with 25 μl of 4M NaOH and then 25 μl of 10% (w/v) aqueous sodium dodecyl sulphate. 100 μl of 4.5M sodium acetate (pH 4.8) were then mixed with the cell lysate. 550 μl of 1 mg/ml FMP particles (Amersham International plc.) in isopropanol were then mixed with the salt-treated cell lysate. The samples were left for 5 minutes at room temperature. The samples were then magnetically separated and the supernatants were then removed to waste. The samples were washed with 500 μl of 80% ethanol. The samples were again magnetically separated and the supernatants were once more removed to waste. The samples were resuspended in 50 μl of TE buffer [1] containing 0.1 mg/ml RNase. The samples were finally magnetically separated and the supernatants were transferred to a microtitre plate. The 50 μl of sample was mixed with 20 μl of gel loading dye [1] and 20 μl loaded on a 1% agarose gel prestained with ethidium bromide.

Samples 17 and 18

500 μl of HB101 cells containing pBluescript were treated as described on pages 1.25 to 1.28 of reference 1 with final resuspension 50 μl of TE buffer [1] containing 0.1 mg/ml RNase by vortex mixing. The 50 μl of sample was mixed with 20 μl of gel loading dye [1] and 20 μl loaded on a 1% agarose gel prestained with ethidium bromide.

Results

In each of lanes 1 to 16 of the resulting gel, two lines were clearly visible, representing plasmid DNA and strand-separated plasmid DNA. In lanes 1, 2, 5, 6, 9, 10, 13 and 14, the plasmid DNA line was the stronger; in lanes 3, 4, 7, 8, 11, 12, 15 and 16, the strand-separated plasmid DNA line was the stronger. In lanes 17 and 18, a single line corresponding to double-stranded plasmid DNA was visible.

REFERENCES

[1] Molecular Cloning, A Laboratory Manual, 2nd edition, J. Sambrook, E. Fritsch and T. Maniatis, Cold Spring Harbour Laboratory Press, 1989.
[2] Chapter 3 of reference 1.
[3] H. Birnboim and J. Doly, NAR., 7, 1513, 1979
[4] D. Holmes and M. Quigley, Anal. Biochem., 114, 192, 1981

We claim:

1. A method of recovering a first molecular species from a starting liquid containing in solution the first molecular species in admixture with a second molecular species, which method comprises the steps of:

precipitating the second molecular species to form an aggregated precipitate of the second molecular species in the liquid, adding magnetically attractable beads to form a suspension of the beads in the liquid, precipitating the first molecular species to form an aggregated precipitate of the first molecular species which entraps the magnetically attractable beads, applying a magnetic field to draw down the magnetically attractable beads and the associated aggregated precipitate of the first molecular species, removing the supernatant liquid containing the aggregated precipitate of the second molecular species.

2. A method as claimed in claim 1, wherein the first molecular species comprises plasmid DNA and the second molecular species comprises other cellular material.

3. A method as claimed in claim 2, wherein the starting liquid is provided by adding alkali alone or alkali and detergent to a suspension of plasmid-containing bacterial host cells so as to lyse the cells.

4. A method as claimed in claim 1, wherein the magnetically attractable beads are added to the liquid together with a precipitant for the first molecular species.

5. A method as claimed in claim 2, wherein the first molecular species comprises strand separated plasmid DNA.

6. A method as claimed in claim 1 of recovering plasmid DNA from a bacterial cell lysate, which method comprises the steps of: p1 adding salt to the bacterial cell lysate to form an aggregated precipitate comprising chromosomal DNA, adding magnetically attractable beads to form a suspension of the beads in the lysate, adding a nucleic acid precipitation reagent to form an aggregated precipitate comprising the plasmid DNA which entraps the magnetically attractable beads, applying a magnetic field to draw down the magnetically attractable beads and the associated aggregated precipitate comprising the plasmid DNA, removing the supernatant liquid containing the aggregated precipitate comprising chromosomal DNA.

7. A method as claimed in claim 6, wherein the aggregated precipitate comprising plasmid DNA is washed and re-suspended in a liquid medium in which it is soluble.

* * * * *